United States Patent [19]

Clemens

[11] 4,156,620
[45] May 29, 1979

[54] APPARATUS AND METHOD FOR CLEANING TEETH

[76] Inventor: George S. Clemens, 255 Dickens St., Northfield, Ill. 60093

[21] Appl. No.: 801,076

[22] Filed: May 27, 1977

Related U.S. Application Data

[63] Continuation-in-part of Ser. No. 489,812, Jul. 18, 1974, abandoned.

[51] Int. Cl.² .................... B08B 7/100; A46B 13/100
[52] U.S. Cl. .......................................... 134/6; 15/22 A
[58] Field of Search ............ 134/1, 6; 15/22 R, 22 A, 15/22 C, 28, 32; 74/29, 30; 310/80

[56] References Cited

U.S. PATENT DOCUMENTS

| | | | |
|---|---|---|---|
| 793,587 | 6/1905 | Johnson | 15/22 A |
| 1,476,433 | 12/1923 | Vandervoort | 15/22 A |
| 1,557,244 | 10/1925 | Domingue | 15/28 |
| 1,712,579 | 5/1929 | Nichols | 15/22 A |
| 2,140,307 | 12/1938 | Belaschk et al. | 15/22 R |
| 2,215,031 | 9/1940 | Elmore | 15/28 |
| 2,598,275 | 5/1952 | Lakin | 74/36 |
| 2,682,066 | 6/1954 | Keely | 15/22 |
| 2,799,878 | 7/1957 | Brausch | 15/22 |
| 3,103,679 | 9/1963 | Clemens | 15/167 |
| 3,178,754 | 4/1965 | Cleverdon | 15/344 |
| 3,242,516 | 3/1966 | Cantor | 15/28 |
| 3,400,417 | 9/1968 | Moret | 15/22 R |
| 3,577,579 | 5/1971 | Duve et al. | 15/22 |

FOREIGN PATENT DOCUMENTS

| | | | |
|---|---|---|---|
| 634607 | 8/1936 | Fed. Rep. of Germany. | |
| 1114464 | 10/1959 | Fed. Rep. of Germany. | |
| 2215799 | 10/1972 | Fed. Rep. of Germany. | |
| 2263432 | 5/1974 | Fed. Rep. of Germany. | |
| 480510 | 3/1954 | Italy | 74/29 |
| 1081021 | 8/1967 | United Kingdom. | |

Primary Examiner—S. Leon Bashore
Assistant Examiner—Chris Konkol
Attorney, Agent, or Firm—James P. Hume; Gary M. Ropski

[57] ABSTRACT

An apparatus and method for cleaning surfaces and crevices of teeth wherein at least one tuft of filaments is rotated in a controlled reciprocating manner whereby the tuft is rotated a number of revolutions in one direction and then rotated the same number of revolutions in the opposite direction. An alternative embodiment comprises a plurality of tufts of filaments, each of which is rotated in a controlled reciprocating fashion about its own central axis. Furthermore, immediately adjacent tufts are contrarotated. Each tuft is rotated about its own central axis, and placed in contact with the teeth whereby the filaments develop a twisting action dynamically and serially progressing from the base of each tuft to the opposite free ends of the filaments. The plurality of tufts are positioned in two parallel rows, each of which has adjacent tufts staggered with respect to each other.

20 Claims, 12 Drawing Figures

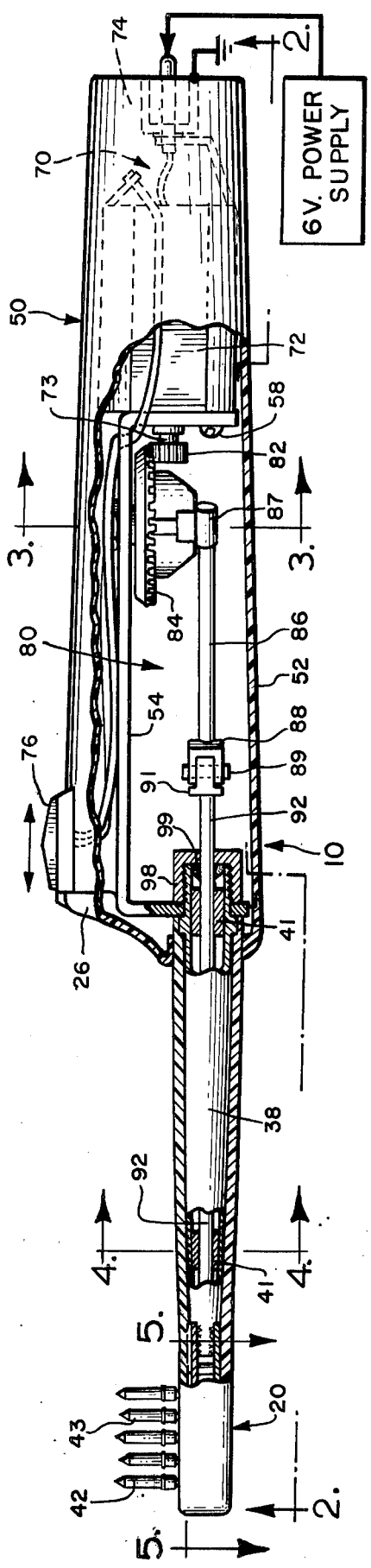
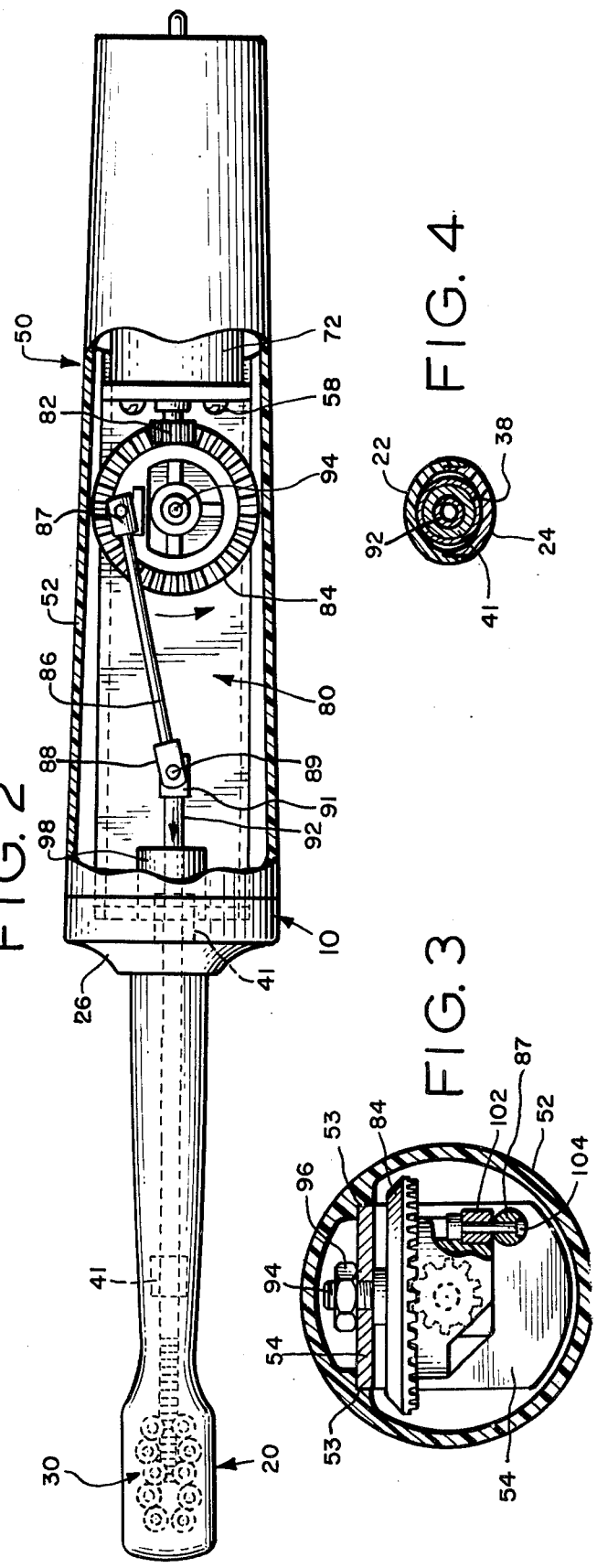

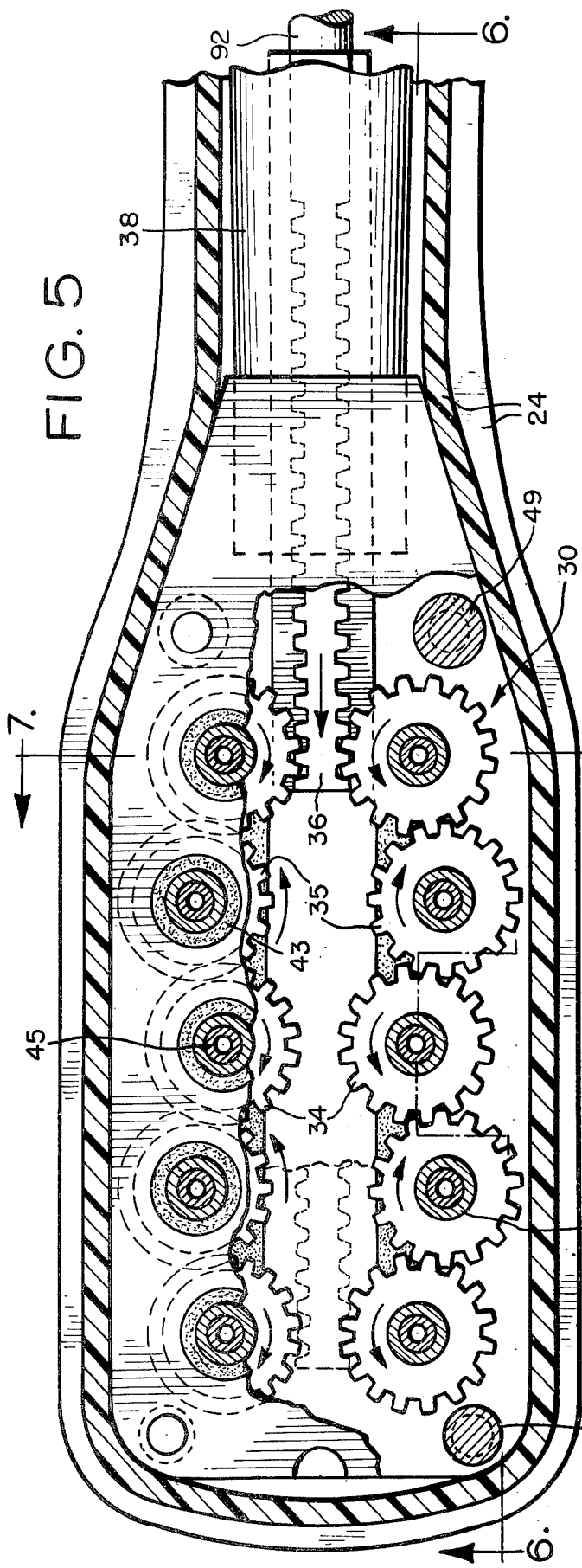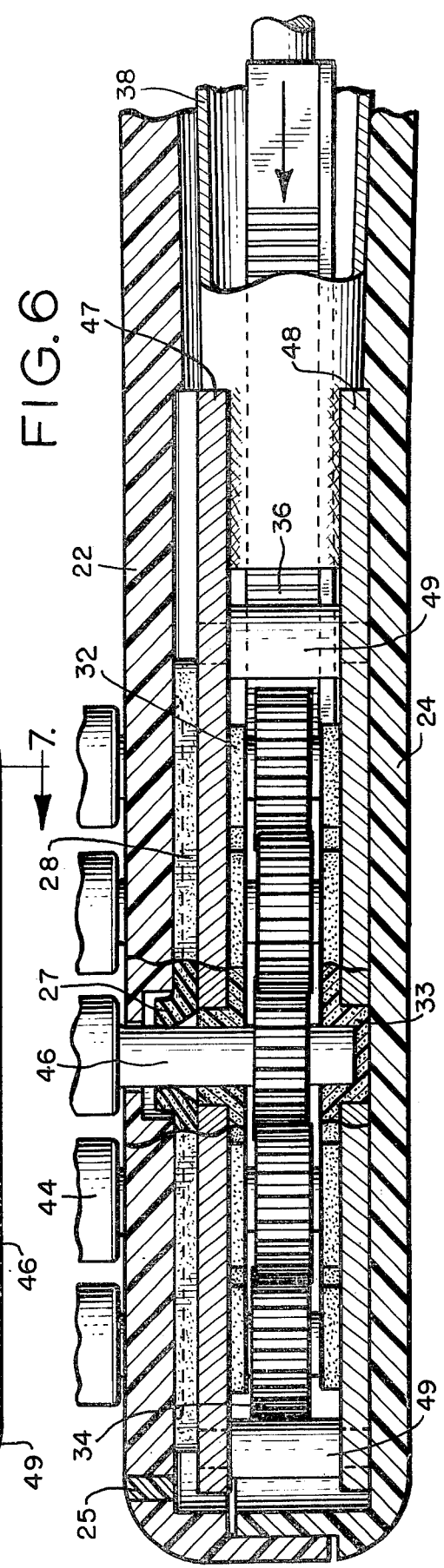

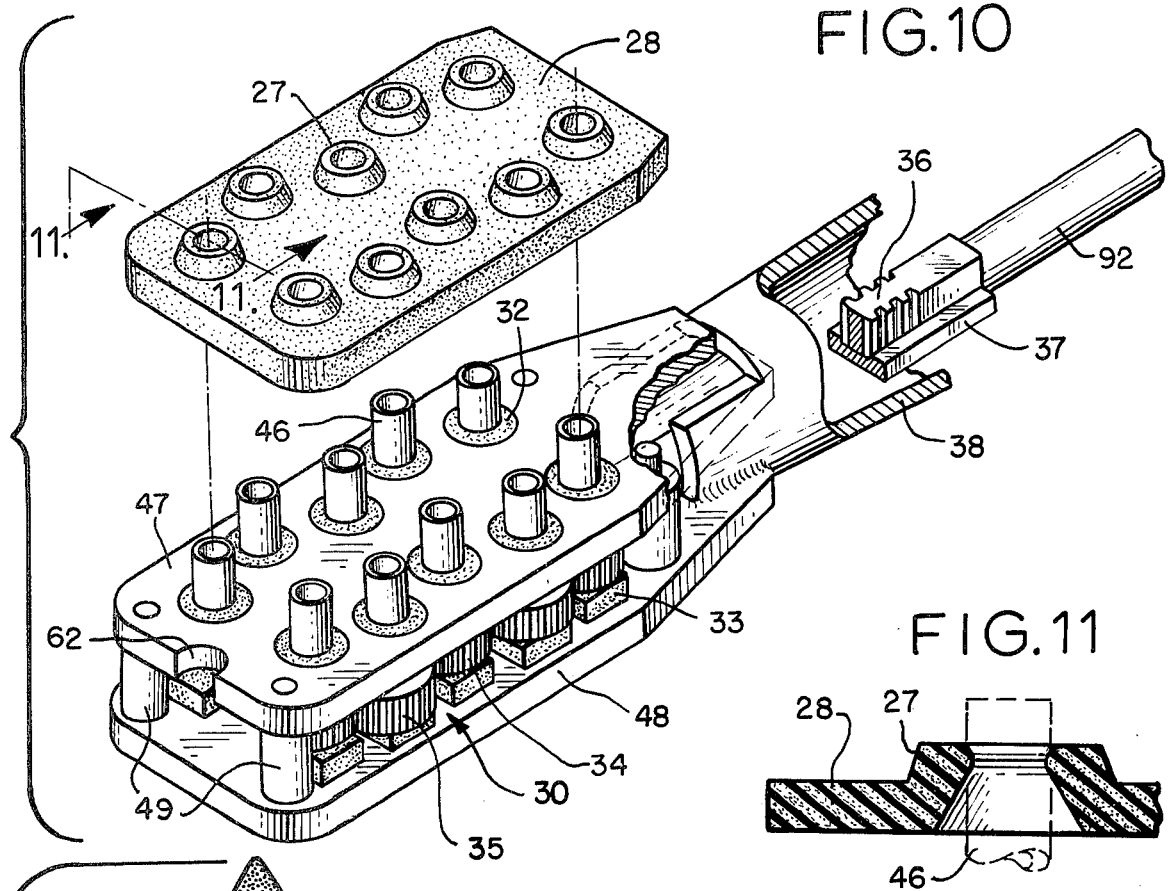
FIG.10
FIG.11
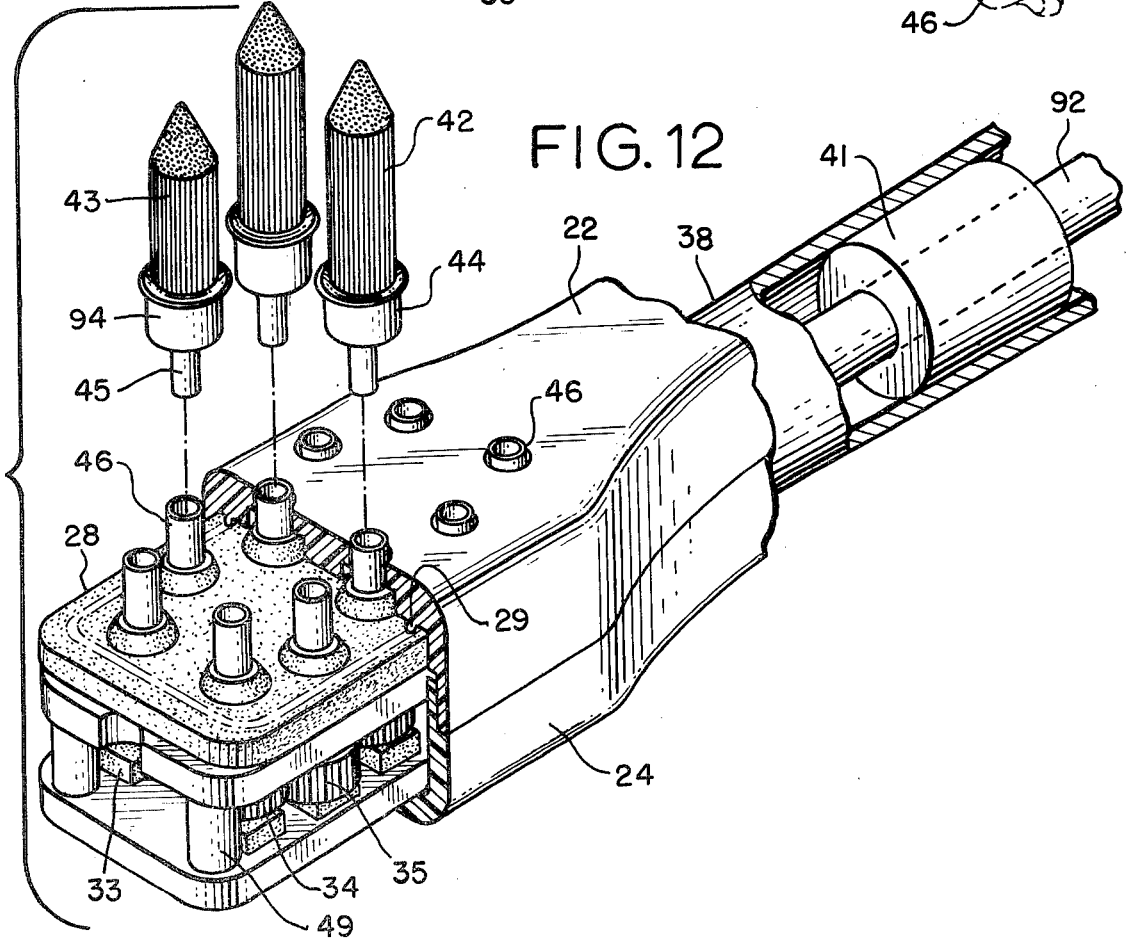
FIG.12

APPARATUS AND METHOD FOR CLEANING TEETH

This is a continuation-in-part of application Ser. No. 489,812 filed July 18, 1974, now abandoned.

BACKGROUND OF THE INVENTION

The present invention involves an improved apparatus and method for cleaning surfaces and crevices of teeth. The purpose of this cleaning is to remove dental plaque which indirectly gives rise to both caries and periodontal disease.

In the prior art, apparatus and methods for brushing teeth are generally divided into three broad categories. The first consists of non-powered brushes in which a number of tufts composed of individual bristles are anchored in a brush head and the movement of the bristles with respect to the teeth is accomplished by physically moving the brush head by hand. The second consists of powered brushes in which the brush head, composed of tufts and bristles similar to those used in hand brushes, is moved in rotary, arcuate, reciprocating, or orbital paths by the power mechanism and in larger paths by hand movement. The third consists of powered brushes in which the brush head is substantially stationary and individual tufts are mechanically rotated unidirectionally each along its own axis.

With conventional hand brush practices, when surface areas and crevices of teeth are involved, cleaning of the smooth facial and lingual surfaces of the teeth is relatively easy because the tips of the bristles in a tuft move with little or no restriction across these broad areas or surfaces. However, approximately ninety percent of the incidence of caries and seventy percent of the incidence of periodontal disease occurs in the interproximal crevices along the mesial and distal surfaces, or the pits and fissures of the occlusal surfaces. In cleaning these areas, the tips of the bristles generally pass over these indentations or recesses. If the bristles are forced into the indentations, they tend to wedge against each other because of their flexibility and length, and assume a static posture which is relatively inefficient for removal of adhesive dental plaque from the indentations. Wedging of the bristles in the indented or recessed areas, as noted above, is due to the fact that the bristles of the tufts are relatively long and flexible. Furthermore, the characteristic flexibility of the individual bristles physically defines a structure which is capable of transmitting to the bristle tips only a very small portion of the motion or power generated at the anchor position of the bristles with the brush head.

Powered brushes of the second category set forth above, such as disclosed in U.S. Pat. No. 3,577,579 issued to Duve et al., are not as effective as the apparatus and method of the present invention because the powered brushes use brush structures similar to conventional hand brushes. In other words, these powered brushes typically do not overcome the disadvantages of the brush structures, including wedging of the bristles and ineffective transmission of power from the brush head to the bristle tips.

Powered toothbrush apparatus of the third category, such as the power driven toothbrush disclosed in U.S. Pat. No. 2,215,031 issued to N. Elmore, generally include means for rotating each of the individual tufts of the brush head continuously in one direction. Because of this unidirectional rotation, the individual tufts of these bristles easily "run-out" of crevices between large surfaces of teeth. This phenomenon is analgous to the characteristic "running-out" of a conventional power drill bit when it is either placed in an irregularly shaped starting opening, or tilted at an angle not normal to the surface to be drilled. In the mouth, the interproximal crevices are irregularly shaped openings, and it is difficult to insert the tufts of a straight-headed brush into the crevices at right angles due to the curvature of the dental arch. This tendency to move out of a crevice or indentation impairs the cleaning efficiency of the toothbrush because the tuft is difficult to position within a crevice for an amount of time adequate to achieve removal of foreign matter desposited within the crevice.

SUMMARY OF THE INVENTION

According to the present invention, an apparatus and method are provided which overcome the disadvantages of the prior art in cleaning tooth crevices and surfaces. The apparatus of the present invention includes a brush head with at least one tuft of filaments rotatably mounted in the brush head. Means are provided for rotating the tuft about its central axis in a controlled reciprocating manner whereby the tuft is rotated a number of revolutions in one direction and then rotated the same number of revolutions in the opposite direction.

According to an alternative preferred embodiment of the present invention, there is provided a plurality of tufts of filaments and each of the tufts is rotated about its own axis in a controlled and predetermined manner. In particular, each tuft is rotated in a controlled reciprocal fashion and immediately adjacent tufts are contrarotated. Furthermore, the tufts are arranged in two parallel rows, each of which has adjacent tufts which are not only staggered but also of varying height with respect to each other.

According to the method of the present invention, there is provided a method for cleaning surfaces and crevices of teeth using a plurality of filaments and at least one tuft configuration wherein the filaments are held together at one end, comprising the steps of placing the tuft on an exposed tooth surface, rotating the tuft about its central axis in a first direction from a neutral position of maximum projected tuft length to a position of maximum filament twist so that the projected length of the tuft diminishes and the tuft is stiffened for effective power transmission, and reciprocally rotating the tuft about its central axis from the position of maximum filament twist. The last step of reciprocal rotation moves the filaments in each reciprocating cycle from a position of maximum twist in a first direction and a minimum projected length to a position of maximum twist in a second direction and the same minimum projected length and then back to a position of maximum twist in a first direction and a minimum projected length while twice passing through a neutral position of maximum projected length. In this manner, the tufts produce both an axially oscillating cleaning motion of the filament tips and a circular sweeping cleaning motion as free ends of the filaments are flared to sweep along crevices between the gingiva and the teeth.

A further alternative embodiment of the method of the present invention provides a method for cleaning surfaces and crevices of teeth using a plurality of filaments and a plurality of tuft configurations wherein the tufts are rotatably mounted so that each of the tufts contrarotates with respect to an adjacent tuft. Each of the tufts is rotated about its central axis in a controlled reciprocating manner whereby each of the tufts is rotated a number of revolutions in one direction and then rotated the same number of revolutions in the opposite direction. The rotating tufts are contacted with tooth surfaces and crevices to be cleaned.

In the apparatus and method of the present invention, rotation about the central axis of a tuft comprised of a plurality of filaments produces a twisting of the filaments with respect to a holder for each tuft. This twisting is a result of the multi-dimensional flexure and elastomeric characteristics of each filament and of the fact that the filaments are held together only at a base end with the other end free for contacting a tooth surface or crevice to be cleaned. As a result of this twisting action, the surfaces of the filaments compress against each other, and as the twisting action moves axially outwardly along each tuft, the tuft becomes increasingly rigid and successively greater energy is transmitted from the tuft holder along the tuft to be dissipated at the filament tips. This energy transmission occurs more effectively than in the prior art apparatus even if the filament tips are confined within the pits and fissures of the occlusal surfaces or in the interproximal crevices between the mesial and distal surfaces of the teeth.

To enable confining of the tufts within the interproximal crevices for a period long enough to attain thorough cleaning, each individual tuft is reciprocally rotated. The rotation is commenced in one angular direction for a distance sufficient to produce both effective energy transfer and lateral movement of the tuft across the interproximal crevice to clean both approximal (mesial and distal) surfaces, but less than the amount which would give rise to "run-out" of the tuft and expulsion from the interproximal crevice. Then each tuft is rotated in the opposite angular direction, again just far enough to produce the same cleaning results with effective energy transfer while avoiding expulsion of the tuft from the crevice.

In order to ensure maximum penetration into the interproximal crevices and to provide a tuft structure having a relatively large number of filaments in contact with the curved mesial and distal surfaces the filaments are arranged so that the tip or "working end" of each tuft is tapered to a moderately sharp configuration. Furthermore, the tip of each filament is provided with a taper so that each filament more easily penetrates into interproximal crevices.

In addition to the mesial and distal surfaces noted above, each tooth has a facial and a lingual surface, all four of which define the vertical surfaces of a tooth crown. Because the gingival margins of the interproximal crevices, usually defined by the interdental papilla, and the gingival margins of the raised facial and lingual tooth surfaces between the approximal surfaces are vertically staggered, the tufts are also preferably arranged in a staggered relationship in each row of tufts. A first set of long tufts are positioned along a first line in the brush head and a second set of shorter tufts are positioned along a second line in the brush head parallel to and spaced from the first line. Within this staggered arrangement the long tufts reach into interproximal crevices of the teeth, and the shorter tufts clean the raised face areas of the teeth near the gingiva.

Another desirable characteristic of the brush of the present invention is that there is no violent or vibratory movement of the brush head itself. Therefore, the brush head can be moved slowly and gently over the tooth surfaces and adjacent gingiva. The entire head of the brush does not oscillate, rotate, move in circular or elliptical paths, or become involved in any movement other than that imparted by the user. This characteristic is particularly important in cleaning teeth because the amount of cleaning motion that can be imparted to a moving brush head cannot be large enough to cause so-called "cheek shake" by action of the brush head in moving against the inner surfaces of the cheek. The present invention avoids these limitations on cleaning motion because the apparatus can be designed so that the tufts rotate at a desired speed for effective cleaning without powered brush head motion.

A further advantage of the present invention is an improved cleaning of the area of the tooth at or near the gingival margins. The reciprocal rotation of each tuft, whereby a tuft rotates first in one direction and then in the other direction, causes flaring of the tips of the filaments so that the filaments tips sweep along the crevice between the gingiva and the teeth. This improved cleaning contributes to placing and maintaining the gingiva in a healthy condition.

Furthermore, as the individual tufts are reciprocally rotated, the tuft filaments are cyclically twisted to form right- and left-handed helices. This twisting causes a change in the overall projected length of each tuft whereby a type of pumping action is produced against the surfaces of the teeth to enhance removal of plaque.

Accordingly, it is a primary object of the present invention to provide an improved apparatus and method for cleaning teeth wherein a plurality of tufts rotating in a controlled reciprocating manner are used to allow the tips of the tuft filaments to be easily positioned and maintained within the interproximal crevices of the teeth.

Another object of the invention is to provide an improved apparatus and method for cleaning teeth wherein a plurality of tufts rotating in a controlled reciprocating manner are utilized to accomplish efficient power transfer from a rotating means in the brush head, through tuft holders and the body of the tuft to the tips of the filaments.

A further object of the present invention is to provide a tooth-cleaning apparatus with a plurality of tufts rotating in a reciprocating manner whereby the filaments are cyclically flared but the tufts and the filaments maintain their original compact shape over a relatively long period of use, and wherein the apparatus is economical to manufacture and easy to use and maintain.

A still further object of the present invention is to provide a tooth-cleaning apparatus including a plurality of long and short tufts which are arranged in a staggered relationship to effectively accomplish cleaning of interproximal crevices and raised tooth faces which are offset from those crevices.

Other objects, features, and advantages of the invention will become apparent upon reading the following detailed description in conjunction with the accompanying drawings.

BRIEF DESCRIPTION OF THE DRAWINGS

FIG. 1 is a partially-sectioned side view of the tooth-cleaning apparatus of the present invention, illustrating the drive and transmission means of the apparatus;

FIG. 2 is a partially-sectioned bottom view of the tooth-cleaning apparatus of FIG. 1 taken along line 2—2 and further illustrating the drive and transmission means of the apparatus;

FIG. 3 is a cross-sectional view of the tooth-cleaning apparatus of FIG. 1 taken along line 3—3 and further illustrating the transmission means of the apparatus;

FIG. 4 is a cross-sectional view of the tooth-cleaning apparatus of FIG. 1 taken along line 4—4 and illustrating a support for the rack drive shaft of the apparatus;

FIG. 5 is an enlarged, partially sectioned top view of the brush head of the tooth-cleaning apparatus of FIG. 1 taken along line 5—5 and illustrating the gear-rack assembly of the apparatus;

FIG. 6 is a cross-sectional side view of the brush head of FIG. 5 taken along line 6—6, illustrating the tuft arrangement and further illustrating the gear-rack assembly of the apparatus;

FIG. 10 is a partially-exploded perspective view of the brush head of the apparatus of the present invention particularly illustrating a unitary seal for tuft drive shafts of the apparatus;

FIG. 11 is a cross-sectional view of the unitary seal shown in FIG. 10 taken along line 11—11 and illustrating the size of the unitary seal aperture in relation to a shaft accommodated therein;

FIG. 12 is a partially exploded perspective view of the brush head of the apparatus of the present invention illustrating the relationship of the brush head casing to the unitary seal and the rest of the gear-rack assembly.

DESCRIPTION OF THE PREFERRED EMBODIMENT

Figure 7:
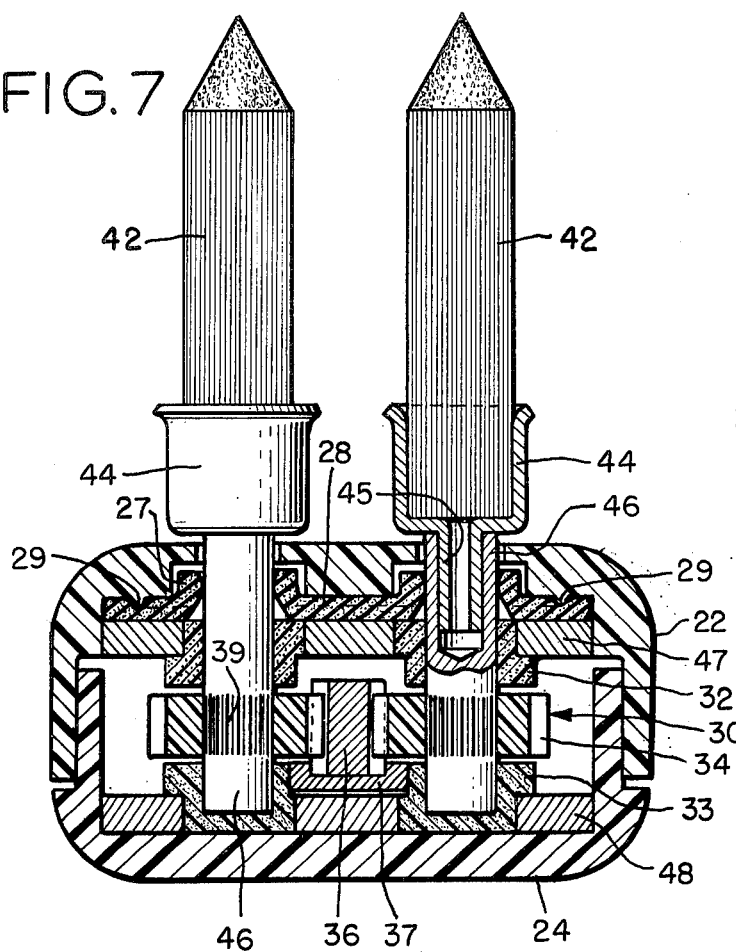
FIG. 7 is a cross-sectional view of the brush head of FIG. 6 taken along line 7—7 and further illustrating the gear-rack assembly of the apparatus.

Referring now to the drawings, and more particularly to FIGS. 1 and 2 there is illustrated in cross-sectional view an embodiment of the apparatus of the present invention, indicated generally by reference numeral 10, and particularly adapted for cleaning surfaces and crevices of teeth for the removal of dental plaque. The areas of the teeth which this preferred embodiment is particularly suited for cleaning include the smooth surfaces of the teeth, the occlusal indentations, and the interproximal crevices.

The toothbrush 10 includes a brush head 20 at one end of the toothbrush 10, and a power handle 50 at the other end. The power handle 50 includes a drive means 70 and a transmission means 80 interconnecting the brush head 20 and the drive means 70. The brush head 20 includes a plurality of long tufts 42 and short tufts 43 each of which is rotatably about its own central axis. In the preferred embodiment ten tufts are arranged in the brush head 20: six long tufts 42 and four short tufts 43. The tufts 42 and 43 are staggered along the brush head 20 to provide improved cleaning of both the interproximal tooth crevices and the facial and lingual tooth surfaces which are raised above and are located between the approximal surfaces. The improved cleaning with the staggered tufts results because the gingival margins of these crevices and raised facial and lingual tooth surfaces are physiologically vertically offset with respect to each other.

The gingival margin of the facial and lingual surfaces typically extends closer to the cervical line of the tooth than the gingival margin of the interproximal crevice, which is defined by an interdental gingival tissue or papilla.

The drive means 70 includes a direct current motor 72 and an electrical connector 74. The transmission means 80 accomplishes transmission of mechanical energy from the drive means 70 by a series of gears including a pinion gear 82 and a crown gear 84, to which a crank arm 86 and a clevis 88 are attached. The clevis 88 is pivotally connected to a drive shaft 92 of a gear-rack assembly 30. As shown in FIGS. 2, 5 and 6, the gear-rack assembly 30 transmits the mechanical energy to the tufts 42 and 43 in a controlled reciprocating manner so that the rotation of the tufts is reversed after a predetermined number of revolutions. Furthermore, the tufts are contrarotated, that is, adjacent tufts rotate in opposite directions.

Referring again to FIGS. 1 and 3, the apparatus of the present invention is shown in two cross-sectional views. The power handle 50 is illustrated having an outer casing 52. The casing 52 of the power handle 50 may be formed of any suitable protective material and preferably is constructed from an insulating plastic material which is sufficiently rigid to define means for support of the drive means 70 and transmission means 80 and to protect the user of the apparatus from the action occurring within the power handle 50 when the apparatus is in use.

The casing 52 is defined in a generally elongated tubular shape tapering slightly from one end to the other with the brush head 20 associated with one end of the casing 52 and an electrical connector 74 is preferably a co-axial type plug for making electrical contact with a source of direct current (d.c.) power, such as the six-volt power supply illustrated in block form in FIG. 1. This d.c. power source may be a suitable battery or a transformer-rectifier for alternating current from a household line. An electrical circuit is defined in a well-known manner in which one side of the connector 74 is routed to the d.c. motor 72, and the other side is routed to a switch 76, accommodated in the casing 52, and thence back to the d.c. motor 72 to complete the circuit. The motor 72 is energized when the switch 76 is closed. The switch 76 is any suitable single-pole switch, and in the preferred embodiment the switch 76 is a single-pole sliding conventional knife switch.

An assembly plate 54 is secured within the casing 52 of the power handle 50 by attaching it laterally along its base within channeled shoulders 53 molded in the inner wall of the casing 52. The motor 72 is secured within the power handle 50 by mounting it to an upturned section of the assembly plate 54 and fastening it thereto with machine screws 58.

As shown in FIGS. 1, 2, and 3, the transmission means 80 includes a pinion gear 82 operatively associated with an output shaft 73 of the motor 72. The pinion gear 82 may be press-fitted to the shaft 73 or may be secured to the shaft by any other suitable means to cause the pinion gear to rotate in conjunction with rotation of the shaft 73 during operation of the motor 72.

The transmission means 80 further includes a crown gear 84 rotatably supported by the assembly plate 54 as illustrated in detail in the cross-sectional view of FIG. 3. The crown gear 82 is supported on a mounting pin assembly 94 which fits within an aperture in the assembly plate 54 and is secured thereto by a mounting nut 96.

When the motor 72 is energized and the shaft 73 is rotating, the crown gear 84 will be driven through the pinion gear 82 which is in operative engagement with the toothed portion of the crown gear 82, as illustrated in FIGS. 1 and 2.

To transform the rotational motion of the crown gear 84, into linearly reciprocating motion of a rack 36 and then to reciprocating rotational motion of the tufts 42 and 43, a group of elements of the transmission means 80 are provided as described below. A crank arm 86 is operatively secured at a first end to a portion of the crown gear 84 which is radially displaced from the central axis of the crown gear 84 and at a second end to a gear rack drive shaft 92. The first end of the crank arm 86 includes a connector 87. As illustrated in FIG. 3, the connector 87 is pivotally secured to the crown gear 82 by means of a drive pin 104 inserted through the connector 87 and mounted in an oil-impregnated bearing 102 pressed into a mating recess in the crown gear 82.

The second end of the crank arm 86 is pivotally connected through a clevis 88 and a clevis pin 89 to a clevis shank 91 of the rack drive shaft 92. The clevis 88 is rigidly secured to the end of the arm 86, as illustrated in FIGS. 1 and 2, and is pivotally connected to the shaft 92 by the pin 89 which extends through openings in the terminal portion of the clevis 88 and a mating opening in the clevis shank 91.

It can readily be seen at this stage of description of the apparatus that the rack drive shaft 92 will be caused to move in linearly reciprocating cycles along its longitudinal axis when the motor 72 is energized. This reciprocating motion results from the action of the crank arm 86 moving in a circular path defined by movement of the crown gear 84. The length of the stroke defined in reciprocating movement of the shaft 92 is a function of the radial distance between the center of the crown gear 84 and the central point of attachment of the crank arm 86 to the crown gear 84.

The brush head 20, including the gear-rack assembly 30, are illustrated in FIGS. 5, 6, 7, 8, 10 and 12 of the drawings. In the particular embodiment shown and described for use in cleaning teeth the brush head 20 has 10 tufts. The number of tufts is chosen so that the area defined by the tufts in the brush head 20 is long enough to efficiently clean a number of tooth surfaces and crevices simultaneously and also short enough that the brush head 20 can be accommodated in the arch of the mouth so that the bulk of the cleaning tips of the tufts can be placed in contact with the lingual surfaces of the teeth. Each tuft is similar to the tufts conventionally used in the toothbrush industry, in which a tuft is defined as a cluster of filaments, having the base ends of the filaments anchored in a single hole and the opposite ends of the filaments free. Such tufts are relatively long and thin so that when used in the apparatus and method of the present invention they easily penetrate into the interproximal tooth crevices and accomplish effective power transfer by twisting of substantially all the filaments of each tuft as it is rotated about its own central axis.

The tufts are alternately arranged in two staggered rows of long tufts 42 and short tufts 43. In the preferred embodiment, as illustrated in FIG. 7, the long tufts 42 in each row are indented or positioned closer to the longitudinal axis of the brush head 20 than the short tufts 43 in each row. Both the short tufts 43 and the long tufts 42 have tapered upper surfaces, defined by the tips of the filaments of each tuft. The tapered configuration of the long tufts 42 allows penetration of the long tuft filaments into interproximal crevices.

The short tufts 43 are also tapered or pointed, for at least two reasons. First, if the short tufts 43 were trimmed to have a flat uppermost surface, oscillatory movement sidewise would be undesirably violent and would create mechanical conflict with adjacent tufts. Secondly, variance in depth of the interproximal crevices causes a flat-trimmed tuft to bear too heavily in some cases on the raised facial and lingual tooth surfaces and in other cases to miss them entirely. For these reasons ends of the short tufts 43 are also trimmed to the point or tapered condition schematically illustrated in the drawings.

The staggered relationship of the long tufts 42 and the short tufts 43 with respect to each other is particularly advantageous in the cleaning of tooth surfaces and interproximal crevices. The raised facial and lingual tooth surfaces of the upper and lower teeth typically extend closer to the palate and floor of the mouth, respectively, than the associated interproximal crevices, thereby defining a staggered relationship between the position of each interproximal crevice and the position of the gingival margins of the raised facial and lingual tooth surfaces. Therefore, in the preferred embodiment, the long tufts 42 are positioned for advantageous penetration of filaments into interproximal areas of teeth whereas the short tufts 43 are positioned for cleaning raised tooth face areas.

Each tuft is comprised of a plurality of filaments having a predetermined diameter and physical characteristics so that the desired cleaning action will be realized with the tuft movement of the present invention. In the preferred embodiment herein, each tuft is approximately 0.090 inches in diameter and contains hundreds of filaments, with each filament having a diameter of 0.004 to 0.006 inches. Each tuft is tapered to an included apex angle of about 50 degrees, and each filament is also shaped to have an apex angle of approximately 25 degrees, whereby cleaning of interproximal tooth crevices, gingival crevices, and other small areas is improved.

As illustrated in FIGS. 7 and 12, each of the ten tufts 42 and 43 is mechanically retained in a metal holder 44. The base ends of the filaments which form the base of each tuft 42 and 43 are preferably fused together with a hot platen whereby the filaments are maintained in a desired arrangement. The base end of each tuft is then press-fitted into the holder 44 whereby frictional engagement of the filaments with the inside wall of the holder 44 secures each tuft to the holder 44. Alternately, the filaments may be held together to form a tuft in the tuft holder 44 using conventional methods other than fusing the base ends.

Each holder 44 has a lower extending portion 45 which is adapted to fit within a bore in a tuft drive shaft 46. The holder 44 is secured to the tuft drive shaft 46 by a suitable adhesive. This means of fastening each tuft holder 44 to each drive shaft 46 provides secure interengagement between the two and defines means for positive drive of the tuft holder 44 and tuft drive shaft 46 in unison.

As illustrated in FIGS. 5, 6, 8, and 9, the tuft drive shafts 46 are journaled within the brush head 20 by a top bearing insert 32 attached to a top support plate 47, and a bottom bearing insert 33 attached to a bottom support plate 48. These inserts 32 and 33 are made of a suitable oil-impregnated bearing material. The top bearing insert 32 is provided with apertures and the bottom bearing insert 33 is provided with recesses which cooperate to position the shafts of the long tufts 42 on about 0.294 inch centers to approximate the average spacing between interproximal crevices in teeth, which is about 0.304 inches. Recesses in the bearing inserts 32 and 33 also position the short tufts 43 substantially equidistant from immediately adjacent long tufts 42. An end of each shaft 46 rests against a recess in the bottom bearing insert thus preventing each shaft 46 from moving axially downwardly. Each shaft 46 is prevented from moving axially upwardly by a drive shaft spur gear. An idler spur gear 35 is press-fitted onto each drive shaft 46 associated with a short tuft 43, and a driven spur gear 34 is press-fitted onto each drive shaft 46 associated with a long tuft 42. Knurls 39 are provided on each shaft 46 to ensure secure engagement with each gear 34 and 35.

Figure 9:
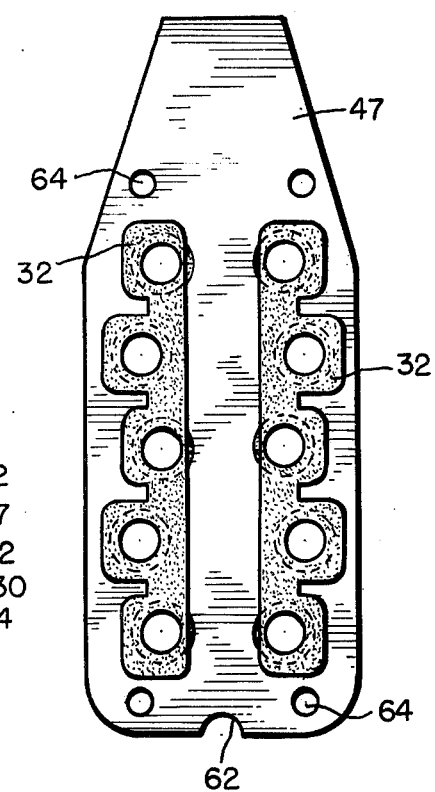
FIG. 9 is a bottom plan view of the brush head of FIG. 8 taken along line 9—9 and illustrating the top support plate and top bearing inserts of the apparatus.
Figure 8:
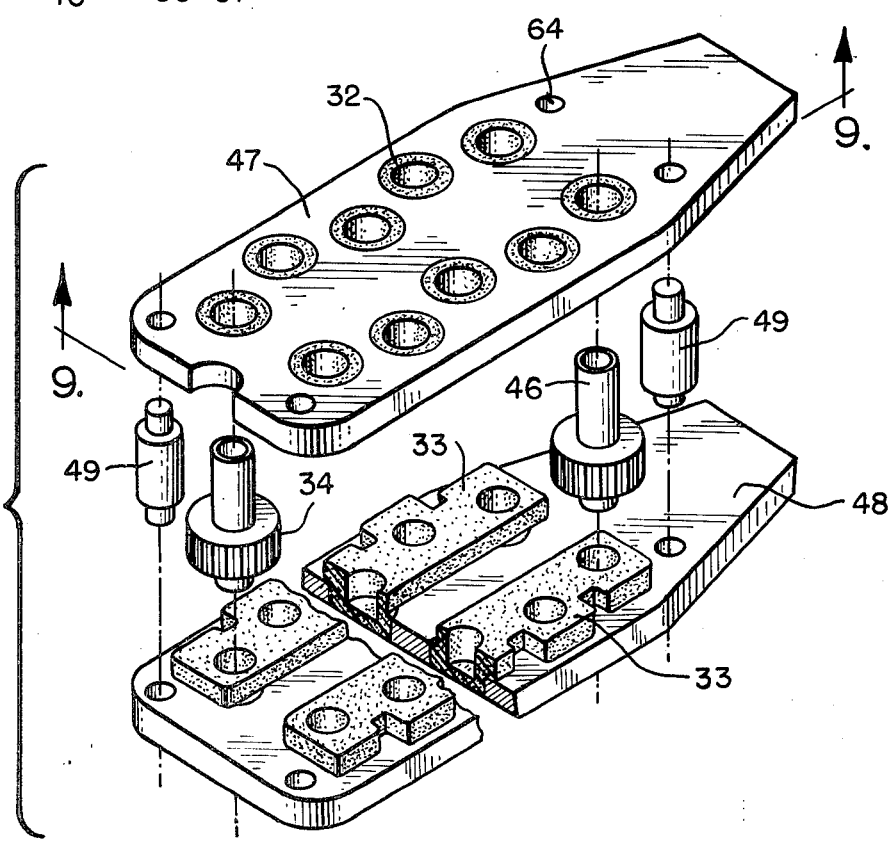
FIG. 8 is an exploded perspective view of the brush head of the apparatus of the present invention further illustrating the gear-rack assembly and the relationship of the various layers of the assembly.

The support plate 47 and 48 are mounted in the brush head 20 and held in rigid inter-relationship with respect to each other by four spacer posts 49 which preferably are provided with turned shoulders at the ends thereof. The posts 49 are inserted into spacer holes 64 and the support plates 47 and 48 rest against the turned shoulders of the posts. After assembly, the ends of the posts 49 inserted into the holes 64 are mechanically expanded or swedged to rigidly secure the plates 47 and 48 thereto. The top support plate 47 is provided with an aperture 62, as shown in FIGS. 9, 10 and 12 for the passage of lubricants therethrough from an oil hole 25 in a top brush head casing 22 to the gear-rack assembly 30.

As was mentioned above, each of the ten tuft drive shafts 46 has a spur gear 34 or 35 connected thereto. The ten spur gears 34 and 35 of the drive assembly are divided into two separate gear trains of five gears each. As illustrated in FIG. 5 the gears are arranged in a staggered fashion so that six driven spur gears 34 mesh with and therefore are driven by the gear rack 36. Moreover, four idler spur gears 35 are driven solely by intermeshing with the driven spur gears 34. In FIG. 5 the gear rack 36 is shown in its most rearward position when it meshes with only two driven spur gears 34, while the eight forward gears continue to rotate as a result of intermeshing of gears. In operation, the rack 36 is reciprocated along a linear path by the gear rack drive shaft 92. Also, in the preferred embodiment, the long tufts 42 and the short tufts 43 have the same base circumference, and the gear rack 36 moves toward the brush head 20 (from the rearward position of FIG. 5) a distance equal to one and one-half times the circumference of each tuft.

Because of the controlled reciprocating linear movement of the gear rack 36, each tuft is rotated in a controlled reciprocating manner for a predetermined cycle. The reciprocating movement in one direction of one and one-half times the base circumference of each tuft is chosen in the preferred embodiment so that each tuft is rotated first one and one-half revolutions in one direction and then one and one-half revolutions in the opposite direction. However, the amount of controlled reciprocating rotation, as measured in units of tuft circumference, may vary in accordance with the diameter of filaments in each tuft, the length and diameter of each tuft itself, and the included angle of the tapered surface of each tuft defined by the tips of the filaments.

In the preferred embodiment, the gear rack 36 is relatively long in comparison to its cross-sectional dimension. In order to reduce the possibility of bending of the gear rack 36 due to the rapid reciprocating forces placed upon the gear rack 36 with this dimensional relationship, the rack is imbedded in and spot-welded to a U-shaped rack plate 37, as shown in FIGS. 7 and 10.

To connect the support plates 47 and 48 to the power handle 50 a metal support tube 38 is provided which encloses the shaft 92. The tube 38 has an exterior wall which tapers in the direction of the brush head 20. At the smaller end of the tube 38, portions of the tube 38 are removed to provide opposing flat surfaces over which the assembled support plates 47 and 48 are fitted and tack-welded or soldered.

As shown in FIG. 1, the tapered support tube 38 is reduced in diameter and threaded at its larger end nearest the power handle 50 so that it may pass through a hole in a turned section of the assembly plate and be fastened thereto by a nut 96. A seal 99 is positioned within the nut 96 to prevent lubricants from the brush head 20 from flowing into the power handle 50.

As shown in FIGS. 1, 3, and 4 the tubular portion of the gear rack drive shaft 92 is supported by and journaled in two oil-impregnated sleeve bearings 41 which are press-fitted into the inside diameter of the tapered support tube 38 which extends between the power handle 50 and brush head 20. In order to protect and isolate the gear-rack assembly 30 of the brush head 20, the shaft 92, and tube 38 there are provided an upper brush head casing half 22 and a lower brush head casing half 24. The casing halves 22 and 24 fit snugly around the support plates 47 and 48 and support tube 38 and are cemented together at matching interfaces to retain lubricants for the gear-rack assembly 30, and to exclude moisture from the environment. At the point where the casing halves 22 and 24 meet an end cap 26 for the housing 52, the casing halves 22 and 24 pass through an aperture in the end cap 26 and a flexible silicon adhesive is applied as a moisture-proof barrier.

In order to ensure retention of lubricants within and exclusion of foreign matter, such as moisture, from the gear-rack assembly 30 there is provided a unitary seal 28 having apertures in which each of the ten drive shafts 46 is fitted. As illustrated in FIGS. 10, 11 and 12, portions 27 of the seal 28 adjacent each tuft drive shaft 46 are elevated and free to move with respect to the base of the seal 28. The flexure of the elevated portions 27 of the seal 28 of the preferred embodiment accommodates tolerance variations in the shaft-hole center-line dimensions of both the bearing insert 32 and the seal 28 itself. A sealing ring 29 in the upper brush head casing 22 abuts the base surface of the seal 28 to prevent liquids from passing around the periphery of the seal 28. FIG. 11 illustrates that each opening of the seal 28 is slightly smaller than necessary to accommodate each shaft 46. Flexure of the seal 28 around and against each tuft drive shaft 46 effects a substantially liquid-tight seal.

It can readily be seen from the foregoing description that in operation of the apparatus of the present invention movement of the switch assembly 76 to energize the motor 72 causes the crown gear 84 to rotate. This, in turn, moves the crank arm 86, causing the gear rack drive shaft 92 to reciprocate, thereby producing a corresponding linear reciprocation of the gear rack 36. As the gear rack 36 moves in a linearly reciprocating path, it meshes with certain of the spur gears 34 in the gear train, rotating them a number of revolutions first in one direction and then a number of revolutions in the opposite direction thereby causing the tufts 42 and 43 associated with the gears 34 and 35 to rotate in a reciprocating manner. During any part of the cycle, except for instantaneous stationary positions, adjacent tufts are rotating in opposite directions.

The desirable speeds for operation of the reciprocating rack 36 are approximately between 800 and 1300 cycles per minute with one and one-half revolutions in each direction per cycle. In the preferred embodiment the rack 36 reciprocates at 1000 cycles per minute and the tufts rotate at approximately 3000 revolutions per minute.

The preferred embodiment of the present invention therefore provides a plurality of tufts which are rotated in a reciprocating manner for approximately one and one-half revolutions in each of two directions. During one half of a reciprocating cycle, each of said first tufts is rotated in a first direction for about one and one-half revolutions while each of said second tufts is rotated in a second direction opposite to the first direction for about one and one-half revolutions, and then, during the other half of the reciprocating cycle, each of said first tufts is rotated in the second direction for about one and one-half revolutions while each of said second tufts is rotated in the first direction for about one and one-half revolutions. This controlled reciprocating rotation of one and one-half revolutions is enough to allow each long tuft 42 to commence some movement within an interproximal crevice by attempting to run out of the crevice along a wall of the crevice. However, the rotation is reversed at an optimum point before run-out and the tuft moves back into and across the interproximal crevice in an attempt to "run-out" along the opposite wall of the crevice. This movement is rapidly repeated to accomplish thorough cleaning of the interproximal crevice and adjacent tooth surfaces. Contrarotation of adjacent tufts according to the invention also assists in improving the stability of the brush for maintaining contact with tooth surfaces and crevices.

The reciprocal rotation of each tuft is also advantageous because it produces flaring of the free ends of the filaments during a part of the reciprocating cycle when the direction of rotation of a tuft is being reversed. Due to their flaring, the extended filament tips sweep along the crevice between the gingiva and the teeth and assist in removing the dental plaque which causes both caries and gingival infection at this point.

The invention provides an improved cleaning apparatus and method which is not only more desirable in use because the tufts themselves move to provide a cleaning action while the brush head remains stationary except for the gentle movement imparted by the user, but also is more efficient and effective due to the particular rotational movement of the tufts and design of the filaments.

Improved cleaning of tooth surfaces is also accomplished by a type of pumping action of the tufts during their reciprocating rotation. As the tufts are moved from a position of maximum rotation in one direction to a position of maximum rotation in the other, there is movement or reorientation among individual filaments from a position of maximum twist in one direction (a shortened helix in one direction) to a neutral position (an extended or straight filament) to a position of maximum twist in the opposite direction (a shortened helix in the opposite direction). A projected length of the filament thus changes from short to longer to short again as the filaments start from a position of maximum twist in one direction and advance to a position of maximum twist in the opposite direction. Such a change in projected length of the filament produces a type of pumping action of the filament tip upon a tooth surface or crevice so that cleaning is improved.

Though the embodiments hereinbefore described are preferred, many modifications and refinements which do not depart from the true spirit and scope of the invention may be conceived by those skilled in the art. It is intended that all such modifications be covered by the following claims.

I claim:

1. An apparatus for cleaning surfaces and crevices of teeth comprising:
    a brush head;
    at least one tuft of filaments, said tuft rotatably mounted in said brush head;
    means for rotating said tuft about its central axis in a controlled reciprocating manner whereby said tuft is rotated a number of revolutions in one direction and then rotated a the same number of revolutions in the opposite direction.

2. The tooth-cleaning apparatus of claim 1 further comprising a plurality of tufts of filaments, each of said tufts being rotatably mounted in said brush head, and wherein said means for rotating each of said tufts about its central axis in a controlled reciprocating manner is adapted to produce contrarotation of each of said tufts with respect to an adjacent tuft.

3. The cleaning apparatus of claim 2 wherein each of said tufts has a tapered surface for cleaning, said surface defined by free ends of the filaments.

4. The cleaning apparatus of claim 3 wherein the free end of each of the filaments is tapered.

5. The cleaning apparatus of claim 2 wherein said means for rotating each of said tufts to produce reciprocating rotation includes a plurality of driven spur gears connected to a group of first tufts, a plurality of idler spur gears connected to a group of second tufts, wherein each of said idler spur gears engages two of said driven spur gears, and a reciprocating rack engaging at least one of said driven spur gears.

6. The cleaning apparatus of claim 5 wherein said first tufts and said second tufts are alternately arranged in two staggered rows of equal length, and the reciprocating rack engages at least two of said driven spur gears.

7. An apparatus for cleaning surfaces and crevices of teeth, comprising:
    a brush head;
    a plurality of first tufts of filaments, each of said first tufts rotatably mounted in said brush head;
    a plurality of second tufts of filaments, each of said second tufts rotatably mounted in said brush head and shorter in length than each of said first tufts, said first tufts and said second tufts alternately arranged in two staggered rows of equal lengths;
    a plurality of driven spur gears, each of which is connected to one of said first tufts;
    a plurality of idler spur gears, each of which is connected to one of said second tufts and meshes with at least two of said driven spur gears whereby each of said first tufts is rotated in a direction opposite each of said second tufts;
    a rack meshing with at least two of said driven spur gears; and
    means for uniformly reciprocating said rack whereby said first tufts and said second tufts are rotated, each about its own central axis, in a controlled reciprocating manner.

8. The tooth cleaning apparatus of claim 7 further including a plurality of tuft drive shafts, each of which is connected to one of said first and second tufts, and a unitary seal having a plurality of apertures to accommodate said tuft drive shafts.

9. The tooth cleaning apparatus of claim 8 wherein the periphery of each of the seal apertures is defined by an elevated portion of the seal extending from the base of the seal whereby flexible sealing contact with said tuft drive shafts is provided.

10. The tooth cleaning apparatus of claim 9 wherein the brush head is provided with an inner surface having a sealing ring for contacting the seal to prevent liquids from flowing past the seal.

11. The tooth cleaning apparatus of claim 7 wherein each of said first tufts and each of said second tufts has a tapered surface for cleaning, said surface defined by the tips of said filaments.

12. The tooth cleaning apparatus of claim 11 wherein the tip of each of said filaments is tapered to define an included angle.

13. The tooth cleaning apparatus of claim 12 wherein the included angle of the tapered tip of each of said filaments is approximately twenty-five degrees.

14. The tooth cleaning apparatus of claim 7 wherein each of said filaments has a diameter of at least about 0.004 inches but not more than about 0.006 inches.

15. The tooth cleaning apparatus of claim 7 wherein said first tufts are arranged on approximately 0.294 inch centers and said second tufts are positioned substantially equidistant from immediately adjacent first tufts.

16. A method for cleaning surfaces and crevices of teeth using a plurality of filaments in a plurality of tuft configurations wherein said tufts are rotatably mounted so that each of said tufts contrarotates with respect to an adjacent tuft comprising:
  rotating each of said tufts about its central axis in a controlled reciprocating manner whereby each of said tufts is rotated a number of revolutions in one direction and then rotated the same number of revolutions in the opposite direction; and
  contacting said rotating tufts with tooth surfaces and crevices to be cleaned.

17. A method of cleaning surfaces and crevices of teeth using a plurality of filaments in a plurality of tuft configurations wherein said tufts are mounted so that each of said tufts contrarotates with respect to each adjacent tuft and wherein each of said tufts is staggered with respect to each adjacent tuft, comprising:
  rotating each of said tufts about its central axis through a controlled reciprocating cycle wherein each of said tufts is rotated about one and one-half revolutions in each of two opposite directions during each cycle;
  contacting said rotating tufts with tooth surfaces and crevices to be cleaned.

18. The tooth cleaning method of claim 17 wherein each of said tufts is rotated at about 3000 revolutions per minute.

19. An apparatus for cleaning surfaces and crevices of teeth, comprising:
  a brush head;
  a plurality of first tufts of filaments, each of said first tufts rotatably mounted in said brush head;
  a plurality of second tufts of filaments, each of said second tufts rotatably mounted in said brush head and shorter in length than each of said first tufts, said first tufts and said second tufts alternately arranged in two staggered rows of equal lengths;
  a plurality of driven spur gears, each of which is connected to one of said first tufts;
  a plurality of idler spur gears, each of which is connected to one of said second tufts and meshes with at least two of said driven spur gears whereby each of said first tufts is rotated in a direction opposite each of said second tufts;
  a rack meshing with at least two of said driven spur gears; and
  means for uniformly reciprocating said rack whereby said first tufts and said second tufts are rotated, each about its own central axis, in a controlled reciprocating manner, said rack reciprocating means including an electrically-powered motor having a rotatable output shaft, a pinion attached to said output shaft in rotary engagement therewith, a crown gear engaging said pinion, a crank arm pivotally and eccentrically attached at a first end to the crown gear, and a rack drive shaft pivotally attached at a first end to a second end of the crank arm, and connected to an end of said rack at a second end of said rack drive shaft.

20. A method of cleaning surfaces and crevices of teeth using a plurality of filaments in at least one tuft configuration wherein the filaments are held together at one end, comprising:
  placing the tuft on an exposed tooth surface;
  rotating the tuft about its central axis in a first direction from a neutral position of maximum projected tuft length to a position of maximum filament twist so that the projected length of the tuft diminishes and the tuft is stiffened for effective power transmission;
  reciprocally rotating the tuft about its central axis from the position of maximum filament twist so that in each reciprocating cycle the filaments move from a position of maximum twist in a first direction and a minimum projected length to a position of maximum twist in a second direction and the same minimum projected length and then back to a position of maximum twist in a first direction and minimum projected length while twice passing through a neutral position of maximum projected length, whereby the tufts produce both an axially oscillating cleaning motion of the filament tips and a circular sweeping cleaning motion as free ends of the filaments are flared to sweep along crevices between the gingiva and the teeth.

* * * * *